(12) United States Patent
Bales et al.

(10) Patent No.: US 8,241,280 B2
(45) Date of Patent: *Aug. 14, 2012

(54) MULTIFILAR FLEXIBLE ROTARY SHAFT AND MEDICAL INSTRUMENTS INCORPORATING THE SAME

(75) Inventors: Thomas O. Bales, Coral Gables, FL (US); Juergen A. Kortenbach, Miami Springs, FL (US)

(73) Assignee: Boston Scientific Scimed, Inc., Maple Grove, MI (US)

( * ) Notice: Subject to any disclaimer, the term of this patent is extended or adjusted under 35 U.S.C. 154(b) by 1308 days.

This patent is subject to a terminal disclaimer.

(21) Appl. No.: 11/854,206

(22) Filed: Sep. 12, 2007

(65) Prior Publication Data

US 2007/0299428 A1    Dec. 27, 2007

Related U.S. Application Data (63) Continuation of application No. 10/856,927, filed on May 27, 2004, now Pat. No. 7,276,067, which is a continuation of application No. 10/155,584, filed on May 24, 2002, now Pat. No. 6,761,717, which is a continuation of application No. 09/418,769, filed on Oct. 15, 1999, now Pat. No. 6,409,727.

(51) Int. Cl.
*A61B 18/14* (2006.01)
(52) U.S. Cl. .......................... 606/47; 606/41
(58) Field of Classification Search ............ 606/41, 606/45–50, 113, 114; 600/562, 564, 566, 600/567; 607/101, 102

See application file for complete search history.

(56) References Cited

U.S. PATENT DOCUMENTS

| | | | |
|---|---|---|---|
| 1,127,948 A | 2/1915 | Wappler |
| 2,036,528 A | 4/1936 | Kesling |
| 2,950,609 A | 8/1960 | Goodloe |
| 3,554,192 A | 1/1971 | Isberner |
| 3,805,770 A | 4/1974 | Okada |

(Continued)

FOREIGN PATENT DOCUMENTS

DE   28 29 159 A1   1/1980

(Continued)

OTHER PUBLICATIONS

Product Brochure, "TRIO 14, Re-Engineering Over-The-Wire Balloon Technology," 4 pages, 1994.

*Primary Examiner* — Michael Peffley
(74) *Attorney, Agent, or Firm* — Seager, Tufte & Wickhem, LLC (57) ABSTRACT

A multifilar flexible rotary shaft includes a plurality of individual filaments which are not wound around each other or around a central core, a loose ensemble of filaments. The input ends of each filament are coupled to each other and the output ends of each filament are coupled to each other. A loose ensemble of N filaments can transmit N times the torque of a single filament, and will have N times the torsional stiffness of a single filament, while retaining the minimum radius of operation of a single filament. Since a loose ensemble of filaments does not have any appreciable contact forces among the filaments (because they are not forcibly twisted together), there is no appreciable internal friction or hysteresis. The filaments should be no more than loosely twisted together, if at all. Several practical applications of the invention are also disclosed.

6 Claims, 3 Drawing Sheets

U.S. PATENT DOCUMENTS

| | | | |
|---|---|---|---|
| 3,895,636 A | 7/1975 | Schmidt | |
| 3,955,578 A | 5/1976 | Chamness et al. | |
| 4,046,150 A * | 9/1977 | Schwartz et al. | 606/127 |
| 4,256,113 A | 3/1981 | Chamness | |
| 4,294,254 A | 10/1981 | Chamness | |
| 4,326,530 A | 4/1982 | Fleury, Jr. | |
| 4,327,711 A | 5/1982 | Takagi | |
| 4,345,599 A | 8/1982 | McCarrell | |
| 4,430,083 A | 2/1984 | Ganz et al. | |
| 4,493,320 A | 1/1985 | Treat | |
| 4,503,855 A * | 3/1985 | Maslanka | 606/47 |
| 4,590,938 A | 5/1986 | Segura et al. | |
| 4,593,680 A | 6/1986 | Kubokawa | |
| 4,619,260 A | 10/1986 | Magill et al. | |
| 4,632,110 A | 12/1986 | Sanagi | |
| 4,706,656 A | 11/1987 | Kuboto | |
| 4,742,817 A | 5/1988 | Kawashima et al. | |
| 4,763,668 A | 8/1988 | Macek et al. | |
| 4,785,825 A | 11/1988 | Romaniuk et al. | |
| 4,790,831 A | 12/1988 | Skribiski | |
| D301,614 S | 6/1989 | Kozak et al. | |
| 4,840,176 A | 6/1989 | Ohno | |
| 4,840,623 A | 6/1989 | Quackenbush | |
| 4,869,238 A | 9/1989 | Opie et al. | |
| 4,872,456 A | 10/1989 | Hasson | |
| 4,905,691 A | 3/1990 | Rydell | |
| 4,945,920 A | 8/1990 | Clossick | |
| 4,950,232 A | 8/1990 | Ruzicka et al. | |
| 4,967,732 A | 11/1990 | Inoue | |
| 4,973,321 A | 11/1990 | Michelson | |
| 5,005,755 A | 4/1991 | Takahashi et al. | |
| 5,026,371 A | 6/1991 | Rydell et al. | |
| 5,059,199 A | 10/1991 | Okada et al. | |
| 5,066,295 A | 11/1991 | Kozak et al. | |
| 5,084,054 A | 1/1992 | Bencini et al. | |
| 5,100,423 A * | 3/1992 | Fearnot | 606/159 |
| 5,114,403 A | 5/1992 | Clarke et al. | |
| 5,125,909 A | 6/1992 | Heimberger | |
| 5,129,913 A | 7/1992 | Ruppert | |
| 5,147,316 A | 9/1992 | Castillenti | |
| 5,147,373 A | 9/1992 | Ferzli | |
| RE34,110 E | 10/1992 | Opie et al. | |
| 5,156,590 A | 10/1992 | Vilmar | |
| 5,158,561 A | 10/1992 | Rydell et al. | |
| 5,163,942 A | 11/1992 | Rydell | |
| 5,176,677 A | 1/1993 | Wuchinich | |
| 5,176,702 A | 1/1993 | Bales et al. | |
| 5,179,935 A | 1/1993 | Miyagi | |
| 5,183,470 A | 2/1993 | Wetterman | |
| 5,201,740 A | 4/1993 | Nakao et al. | |
| 5,201,743 A | 4/1993 | Haber et al. | |
| 5,207,686 A * | 5/1993 | Dolgin | 606/113 |
| 5,244,619 A | 9/1993 | Burnham | |
| 5,254,117 A | 10/1993 | Rigby et al. | |
| 5,254,130 A | 10/1993 | Poncet et al. | |
| 5,279,280 A | 1/1994 | Bacich et al. | |
| 5,281,220 A | 1/1994 | Blake, III | |
| 5,281,230 A | 1/1994 | Heidmueller | |
| 5,290,294 A | 3/1994 | Cox et al. | |
| 5,313,943 A * | 5/1994 | Houser et al. | 600/374 |
| 5,318,564 A | 6/1994 | Eggers | |
| 5,334,169 A | 8/1994 | Brown et al. | |
| 5,336,227 A | 8/1994 | Nakao et al. | |
| 5,358,493 A | 10/1994 | Schweich, Jr. et al. | |
| 5,366,443 A | 11/1994 | Eggers et al. | |
| 5,376,094 A | 12/1994 | Kline | |
| 5,403,342 A | 4/1995 | Tovey et al. | |
| 5,404,887 A | 4/1995 | Prather | |
| 5,406,939 A | 4/1995 | Bala | |
| 5,439,478 A | 8/1995 | Palmer | |
| 5,465,710 A | 11/1995 | Miyagi et al. | |
| 5,486,182 A | 1/1996 | Nakao et al. | |
| 5,496,292 A | 3/1996 | Burnham | |
| 5,501,692 A | 3/1996 | Riza | |
| 5,542,948 A | 8/1996 | Weaver et al. | |
| 5,584,843 A | 12/1996 | Wulfman et al. | |
| 5,588,964 A | 12/1996 | Imran et al. | |
| 5,591,202 A | 1/1997 | Slater et al. | |
| 5,601,533 A | 2/1997 | Hancke et al. | |
| 5,636,634 A | 6/1997 | Kordis et al. | |
| 5,642,736 A | 7/1997 | Avitall | |
| 5,647,846 A | 7/1997 | Berg et al. | |
| 5,681,296 A | 10/1997 | Ishida | |
| 5,685,822 A | 11/1997 | Harhen | |
| 5,685,853 A | 11/1997 | Bonnet | |
| 5,718,360 A | 2/1998 | Green et al. | |
| 5,741,271 A | 4/1998 | Nakao et al. | |
| 5,746,747 A | 5/1998 | McKeating | |
| 5,755,724 A | 5/1998 | Yoon | |
| 5,759,187 A | 6/1998 | Nakao et al. | |
| 5,762,631 A | 6/1998 | Klein | |
| 5,766,217 A | 6/1998 | Christy | |
| 5,769,841 A | 6/1998 | Odell et al. | |
| 5,792,116 A | 8/1998 | Berg et al. | |
| 5,800,444 A | 9/1998 | Ridinger et al. | |
| 5,810,802 A | 9/1998 | Panescu et al. | |
| 5,814,052 A | 9/1998 | Nakao et al. | |
| 5,817,111 A | 10/1998 | Riza | |
| 5,820,464 A | 10/1998 | Parlato | |
| 5,820,546 A | 10/1998 | Ouchi | |
| 5,827,177 A | 10/1998 | Oneda et al. | |
| 5,827,272 A | 10/1998 | Breining et al. | |
| 5,846,248 A | 12/1998 | Chu et al. | |
| 5,860,975 A | 1/1999 | Goble et al. | |
| 5,882,347 A | 3/1999 | Mouris-Laan et al. | |
| 5,885,508 A | 3/1999 | Ishida | |
| 5,906,620 A | 5/1999 | Nakao et al. | |
| 5,906,621 A | 5/1999 | Seacrest et al. | |
| 5,951,579 A | 9/1999 | Dykes | |
| 5,954,635 A | 9/1999 | Foley et al. | |
| 5,957,932 A | 9/1999 | Bates et al. | |
| 5,961,511 A | 10/1999 | Mortier et al. | |
| 5,971,994 A | 10/1999 | Fritzsch | |
| 5,984,904 A | 11/1999 | Steen et al. | |
| 5,984,920 A | 11/1999 | Steinbach | |
| 5,989,247 A | 11/1999 | Chambers | |
| 5,993,474 A | 11/1999 | Ouchi | |
| 6,001,096 A | 12/1999 | Bissinger et al. | |
| 6,010,512 A | 1/2000 | Chu et al. | |
| 6,015,381 A | 1/2000 | Ouchi | |
| 6,015,415 A | 1/2000 | Avellanet | |
| 6,024,708 A | 2/2000 | Bales et al. | |
| 6,027,460 A | 2/2000 | Shturman | |
| 6,050,995 A | 4/2000 | Durgin | |
| 6,068,603 A | 5/2000 | Suzuki | |
| 6,071,233 A | 6/2000 | Ishikawa et al. | |
| 6,074,408 A | 6/2000 | Freeman | |
| 6,090,073 A | 7/2000 | Gill | |
| 6,090,129 A | 7/2000 | Ouchi | |
| 6,093,195 A | 7/2000 | Ouchi | |
| 6,224,611 B1 | 5/2001 | Ouchi | |
| 6,235,026 B1 * | 5/2001 | Smith | 606/46 |
| 6,299,612 B1 * | 10/2001 | Ouchi | 606/47 |
| 6,409,727 B1 | 6/2002 | Bales et al. | |
| 6,761,717 B2 | 7/2004 | Bales et al. | |

FOREIGN PATENT DOCUMENTS

| | | |
|---|---|---|
| DE | 36 16 193 A1 | 11/1986 |
| DE | 94 18 834.3 U | 3/1995 |
| DE | 199 53 359 A1 | 5/2000 |
| WO | WO 00/42926 A1 | 7/1900 |
| WO | WO 92/22254 A1 | 12/1992 |
| WO | WO 00/53107 A1 | 9/2000 |
| WO | WO 01/10321 A1 | 2/2001 |

* cited by examiner

Fig. 8

MULTIFILAR FLEXIBLE ROTARY SHAFT AND MEDICAL INSTRUMENTS INCORPORATING THE SAME

CROSS-REFERENCE TO RELATED APPLICATIONS

This application is a continuation of U.S. application Ser. No. 10/856,927, filed May 27, 2004, now U.S. Pat. No. 7,276,067; which is a continuation of U.S. application Ser. No. 10/155,584, filed May 24, 2002, now U.S. Pat. No. 6,761,717; which is a continuation of U.S. application Ser. No. 09/418,769, filed Oct. 15, 1999, now U.S. Pat. No. 6,409,727; the disclosures all of which are incorporated herein by reference.

This application is related to application U.S. application Ser. No. 09/369,724 filed Aug. 6, 1999, now U.S. Pat. No. 6,235,026 and entitled "Polypectomy Snare Instrument," the complete disclosure of which is hereby incorporated by reference herein.

BACKGROUND OF THE INVENTION

1. Field of the Invention

The invention relates to flexible rotary shafts. More particularly, the invention relates to a multifilar flexible rotary shaft having reduced hysteresis, increased torque transmission, and low internal friction. The shaft of the invention is particularly useful as a component of minimally invasive surgical instruments which must traverse a tortuous path.

2. State of the Art

Flexible rotary shafts are used in many applications in order to transmit a torque through a curved path. Generally, a flexible rotary shaft has an input end which is coupled to a source of rotational energy (e.g., a motor) and an output end which is coupled to something to be rotated. In some applications, a single, monofilar, wire is used. A monofilar flexible rotary shaft must have sufficient yield strength to resist permanent distortion when bent around a specified radius of curvature, or "radius of operation". Indeed, when designing a monofilar flexible rotary shaft, the designer must first determine the radius of operation, i.e., the smallest radius the shaft will be expected to traverse. The maximum wire diameter for the radius of operation can be determined solely on the yield strength and modulus of elasticity of the wire used. A wire of a given material having a diameter larger than this maximum would be permanently deformed if bent around the radius of operation.

Once the maximum diameter of a monofilar flexible rotary shaft is determined for a particular radius of operation, the designer must determine whether the wire has strength and torsional stiffness for a particular application. Monofilar flexible rotary shafts are notoriously inadequate for transmitting a relatively large torque through relatively small radius of operation.

Figure 1:
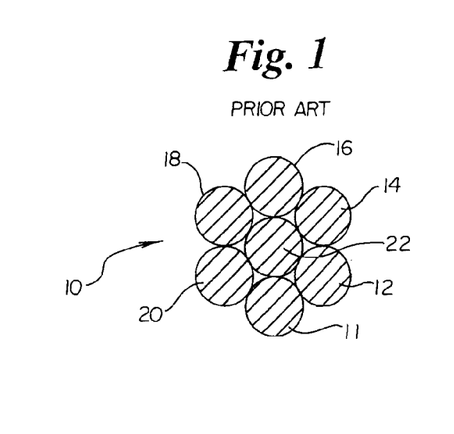
FIG. 1 is a schematic cross-sectional view of a prior art multifilar flexible rotary shaft.
Figure 2:
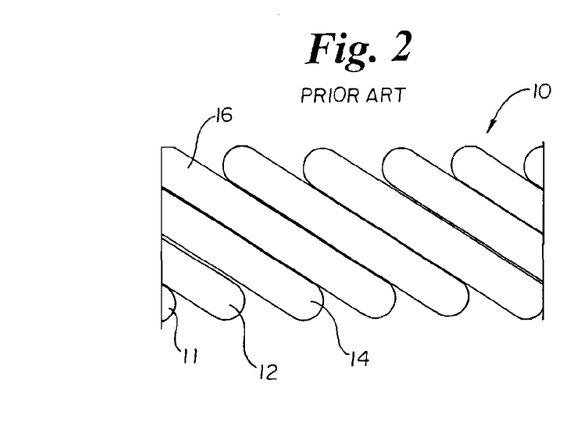
FIG. 2 is a schematic side elevational view of the prior art multifilar flexible rotary shaft of FIG. 1.

Traditionally, multifilar flexible rotary shafts have been employed for transmitting a relatively large torque through relatively small radius of operation. Prior Art FIGS. 1 and 2 illustrate a simple multifilar shaft. A typical multifilar flexible shaft 10 consists of a plurality of wire filaments, e.g., 11, 12, 14 16, 18, 20, wound, typically about a center filament, e.g., 22, in a helical organization. Though not shown in prior art FIGS. 1 and 2, often several layers of filaments are wound in alternating opposite directions. While these constructions overcome the deficiency of monofilar flexible rotary shafts, they nevertheless have their own disadvantages. The most notable disadvantage of multifilar flexible rotary shafts is increased hysteresis which results from internal friction among the filaments. Hysteresis is the term generally used to describe the difference in the behavior of the input and output ends of a flexible rotary shaft. In its simplest form, hysteresis refers to a time delay between the application of torque at the input end and the resulting rotation of the output end. Hysteresis also refers to other, erratic, behavior of the output end which is not identical to the behavior at the input end.

Internal friction and hysteresis in multifilar flexible rotary shafts results from the manner in which they are constructed. Specifically, the individual wires are deformed during the winding process so that they bear against one another in such a way that the assembly "holds itself together." That is, if one disassembles such a flexible shaft, one will find that the individual wires are deformed into a helical shape, and each layer grips the next inner layer with a certain amount of compression. This type of construction is known as a "pre-formed" cable, because the individual wires are formed into helical shapes during the stranding process. If such cables were not made in this way, they would be very difficult to handle as a subassembly because they would spring apart when the ends were cut. In fact, some flexible shafts do spring apart to some extent when cut, but in all known multifilar flexible shafts the individual wires are permanently deformed into a helical shape. Because of this, there are considerable compressive contact forces among the wires, resulting in friction between the wires when the shaft is rotated while traversing a curved path. This internal wire-to-wire friction results in energy absorption in the flexible shaft, so that energy delivered to the output end is less than the energy applied to the input end.

It is known that the filaments of a flexible shaft generate internal friction which increases as its radius of operation decreases. Further, for a given radius of operation, the more flexible the shaft, the lower will be the amount of internal friction. The torque needed to overcome the resistance due to this internal friction is called the "torque to rotate." As such, the torque-to-rotate value of a given shaft is normally specified for a specific radius of operation. It follows, therefore, that the more flexible the shaft, i.e., the higher the bending flexibility, the lower will be the torque to rotate for a given radius of operation.

Torsional stiffness and torsional deflection denote inverse parameters of a flexible shaft. Torsional stiffness specifies a measure of the resistance of the shaft to an applied torque, i.e., a twisting or a torsional force, about its rotational axis. Torsional deflection designates the degree of twist per unit length that a flexible shaft will experience due to an applied torque. The torsional deflection is usually expressed in degrees per foot per pound-inch (deg/ft/lb-in); its inverse, torsional stiffness, is expressed in units of lb-in/ft/deg.

Therefore, when choosing a flexible shaft, the length of the smallest radius of operation and the magnitude of the input torque are important factors in determining the bending flexibility of the shaft. The following conditions should be met when selecting a flexible shaft: first, the shaft must have sufficient bending flexibility so as not to be damaged when flexed into its smallest radius of operation; second, the shaft must have sufficient flexibility so that the torque-to-rotate value at the smallest radius of operation is at least less than the input torque, i.e., the output torque of the driver element; and third, the shaft must have sufficient torsional stiffness to accurately transmit rotary motion with a minimum of torsional deflection.

Most designers believe that the mechanism of torque transmission along a multifilar flexible shaft is by means of tensile (and compressive) stresses in the individual wires. In fact, for existing multifilar flexible shafts transmitting large torques this is essentially true. When subjected to high torques, such multifilar assemblies react by some layers expanding and some contracting (depending upon the direction of twist). If the inner are expanding layers, they are resisted by outer contracting layers, so the torque is resolved into tensile stresses in the contracting layers and compressive stresses in the expanding layers. This reaction to torque thus results in contact forces between the layers of wire, and these contact forces result in friction. As a result, there is noticeable lost rotary motion at the output end of the flexible shaft when the input torque is alternated from one direction to the other, as in the case of a shaft used to steer a medical device or to transmit a rotary position signal. When the input of the shaft is twisted in one direction from its static condition, a certain amount of twist (hysteresis) is required to overcome the internal friction and cause the layers to come into interference with one another before the rotary motion is observed at the output end. If the shaft is then twisted in the alternate direction, the previous hysteresis must first be overcome to return the internal state of the wires to its static condition; then, a similar amount of hysteresis is introduced as the shaft is "wound up" in the new direction. This hysteresis is made worse when the flexible shaft traverses a curved path, because additional stresses between the layers (resulting in increased internal friction) are introduced by the bending of the shaft through a curved path.

The previously described hysteresis in a pre-formed multifilar flexible shaft prevents it from working as a precise transmitter of rotary motion from one end to the other. While these shafts may work well enough in the unidirectional transmission of power, they are ineffective in precisely transmitting rotary control (in two rotational directions) because of the hysteresis or "lost motion" caused by their internal friction.

SUMMARY OF THE INVENTION

It is therefore an object of the invention to provide a flexible rotary shaft which has reduced hysteresis.

It is also an object of the invention to provide a flexible rotary shaft which has increased torque transmission.

It is another object of the invention to provide a multifilar flexible rotary shaft which has little or no internal friction.

It is still another object of the invention to provide a flexible rotary shaft which has accurate torque transmission when reversing from one rotational direction to the opposite rotational direction.

It is a further object of the invention to combine the benefits of a monofilar flexible rotary shaft with the benefits of a multifilar flexible rotary shaft while avoiding the deficiencies of each.

In accord with these objects which will be discussed in detail below, the multifilar flexible rotary shaft of the present invention includes a plurality of individual filaments which are not wound around each other or around a central core. The input ends of each filament are coupled to each other and the output ends of each filament are coupled to each other. Preferably all of the filaments are identical and, for a plurality of N wires, each wire has 1/N the yield stress required to transmit the maximum torque required. While intuitively it seems that the filaments must be twisted together in order to transmit torque, such is not the case. In fact, a group of N filaments can transmit N times the torque that can be transmitted by a single filament (up to its yield stress) even if the wires do not touch one another. Thus, a loose ensemble of N filaments can transmit N times the torque of a single filament, and will have N times the torsional stiffness of a single filament, while retaining the minimum radius of operation of a single filament.

Since a loose ensemble of filaments would not have any appreciable contact forces among the filaments (because they are not forcibly twisted together), there is no appreciable internal friction or hysteresis. In fact, in order to appreciably eliminate all the hysteresis in such an ensemble of filaments, the filaments should be no more than loosely twisted together, if at all. In fact, the only reason for loosely twisting the wires together is to allow the ensemble to be easily handled and to insure that the individual wire filaments follow the same general curved path from one end to the other. However, if the rotary shaft is fabricated to a predetermined length and placed inside a flexible conduit, the filaments may be left completely loose, e.g., laid together in parallel.

The present invention describes a way of constructing a flexible shaft with little or no internal friction. Such a flexible shaft will transmit rotary motion with little or no hysteresis, resulting in a precise transmission of motion from one end to the other, even in cases of reversing rotary motion, and while bent around small radii. In fact, the flexible shaft of the invention can be bent around radii as small as could be negotiated by a monofilar flexible shaft having a diameter equal to the diameter of a single one of the individual filaments.

The invention has many practical applications, particularly in the manufacture of minimally invasive surgical instruments which must traverse a tortuous path. Two particular examples are illustrated herein, i.e., a polypectomy snare instrument and a steerable flexible microsurgical instrument with a rotatable clevis.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 3:
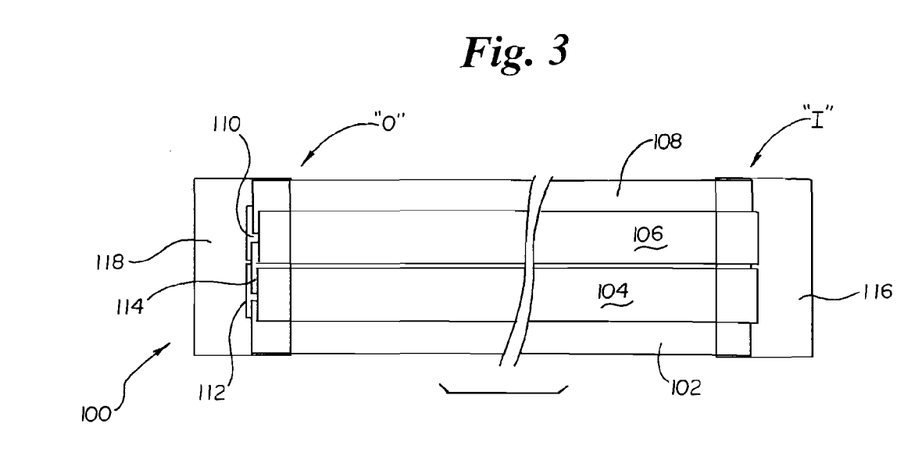
FIG. 3 is a schematic, partially transparent, broken pseudo-perspective view of a multifilar flexible rotary shaft according to the invention.

Referring now to FIG. 3, a multifilar flexible rotary shaft 100 according to the present invention includes a plurality of individual filaments, e.g., 102, 104, 106, 108, 110, 112, 114. Each filament has an input end, designated generally as "I" in FIG. 3 and an output end, designated generally as "O" in FIG. 3. All of the input ends are coupled to each other, for example by a coupling 116. All of the output ends are coupled to each other, for example by a coupling 118. The filaments are not tightly wound around each other or around a central core.

However, they may be wound together loosely merely to facilitate handling of the shaft. Preferably all of the filaments are identical and, for a plurality of N wires, each wire has 1/N the yield stress required to transmit the maximum torque required for the shaft.

Discussion of Physical Principals of the Invention:

If a torque is applied to a free mechanical body, that body will begin to take on an accelerating angular velocity. In order for the body to remain unaccelerated it is necessary for another torque, equal and opposite to the first torque, to be applied to it. It is not necessary that the two equal and opposite torques be applied at the same point on the body. Thus, rigid mechanical bodies effectively "add" or integrate all torques applied to them, and if the body is static (or rotating at a constant angular velocity), it is an unavoidable conclusion that all the torques applied to it sum to zero.

With this in mind, if two rigid free bodies are connected by a single, unsupported, monofilar wire filament, when the first body is rotated while the second body is held fixed, the wire filament is torsionally deformed, resulting in a "reaction torque" at the anchoring point of the second rigid body. Since the wire filament is unsupported, there are no surface contact pressures on it, and hence no frictions resisting its motion or creating any reaction torque in the wire itself. The result is that the reaction torque at the second body is equal in magnitude to the applied torque on the first body. As long as the torsional stresses in the wire filament are below the yield stress of the wire, this system will precisely transmit torque and rotary motion from one end to the other with no hysteresis. This construction is simple and intuitive.

It has been discovered that if a second unsupported monofilar wire filament is coupled between the bodies, each wire acts independently: when the first body is rotated and the second body is held fixed, torques are applied to each of the wires independently. If the wires are the same material, size, and length (and hence, the same torsional stiffness), then the torque on each wire will be half the torque applied to the first body. At the second body, each wire imparts its torque to that body, so that the total torque applied by the two wires to the second body is the same as the torque applied to the first body. This analysis is true if the wires are unsupported and no other forces are acted on them, even if the wires do not touch one another.

While intuitively one assumes that the wires must be twisted together in order to transmit torque, such is not the case. In fact, a group of N wires can transmit N times the torque that can be transmitted by a single wire (up to its yield stress) even if the wires do not touch one another. Thus, a "loose ensemble of N wires" can transmit N times the torque of a single wire, and will have N times the torsional stiffness of a single wire, while retaining the minimum bend radius of a single wire. Since a loose ensemble of wires does not have any appreciable contact forces among the wires (because they are not forcibly twisted together), there is no appreciable internal friction or hysteresis. In fact, in order to appreciably eliminate all the hysteresis in such as ensemble of wires, the wires should not be twisted together at all or at most only loosely twisted together. In fact, the only reason for loosely twisting the wires together is to allow the ensemble to be easily handled and to insure that the individual wire filaments follow the same general curved path from one end to the other.

In a practical construction of a shaft according to the invention described in detail below with reference to FIGS. 4-8, a group (e.g., 3 or 4) of several small diameter (e.g., 0.005" to 0.040") wires are joined at the first end, loosely arranged together (either parallel, loosely twisted, or braided), and then joined at the second end. The junctions at the first and second end of the ensemble serve the functions of the first and second rigid bodies described in the analysis above. If there are N wires in the ensemble, they will have N times the torsional stiffness of a single such wire, and they will be capable of transmitting N times the torque of a single such wire with no appreciable hysteresis. It should be noted that although a loose ensemble of wires makes a very precise transmitter of rotary motion and torque for small torques, it is not generally capable of transmitting as large a torque as a tightly-twisted strand of an equal number of similar wires because there is no way to resolve the torque applied to the first body into tensile stresses and compressive stresses in the wire bundle unless the wires are tightly twisted together so that they interfere with one another. As described below, the practical exemplary embodiments are designed to transmit torques on the order of 0.1 ounce-inch with an operational radius of approximately 0.8 inches.

It should also be noted that there is another advantage to a loose ensemble of wires for transmitting rotary motion or torque around sharp bends. When a tightly twisted strand of wires is used as a flexible shaft, it is usually enclosed inside a tubular sheath to contain the wires and reduce friction. When the sheath is bent around a tight radius, the outer layer of wires must slide along the internal surface of the sheath as the flexible shaft rotates. For a first-order approximation, the contact forces $F_{contact}$ inside the sheath are equal to the stiffness of the tightly wound flexible shaft $S_{flex\ shaft}$ divided by the radius of curvature $R_{curve}$ of the shaft. The reactive torque $T_{r\ (flex\ shaft)}$ created by this contact force is equal to the product of the contact force $F_{contact}$ times the coefficient of friction $C_f$ times the radius of the flexible shaft $R_{s\ (flex\ shaft)}$. Thus, the reaction torque $T_r$ of the tightly wound shaft is defined by:

$$T_{r(flex\ shaft)} = (S_{flex\ shaft}/R_{curve}) * C_f * R_{flex\ shaft} \quad (1)$$

However, in a loose ensemble of wires, when the ensemble is bent around a curve, the wires each assume the maximum possible bend radius; that is, they lay alongside each other on the inside of the sheath. For small amounts of rotation, these individual wires will revolve independently about their own axes rather than whirling around as a group; so, the reactive torque acting on each of them resulting from friction against the sheath would be:

$$T_{r(wire)} = (S_{wire}/R_{curve}) * C_f * R_{wire} \quad (2)$$

where $S_{wire}$ is the stiffness of the wire and $R_{wire}$ is the radius of the wire. So, for an ensemble of N wires, the total reaction torque on the ensemble is equal to:

$$T_{r(ensemble)} = N * (S_{wire}/R_{curve}) * C_f * R_{wire} \quad (3)$$

Thus, the ratio of friction torque for the ensemble and the flexible shaft would be:

$$T_{r(flex\ shaft)}/T_{r(ensemble)} = [S_{flex\ shaft}/N*S_{wire}] * [R_{flex\ shaft}/R_{wire}] \quad (4)$$

For an ensemble and a flexible shaft with the same torsional stiffnesses, the flexural stiffness will also be equal, because the torsional stiffness follows the same formula as the bending stiffness. Thus, the first term on the right side of equation (4) reduces to approximately 1. The result is that the ratio of the friction torques ($T_{r\ (flex\ shaft)}/T_{r\ (ensemble)}$) is equal to the ratio of the radius of the flexible shaft to the radius of the individual wires in the ensemble. So the torque due to friction of a loose ensemble of wires acting as a torque transmitter is smaller than the torque due to the friction of a similarly stiff flexible shaft by the ratio of the diameters. For a typical assembly of seven wires, the ratio of diameters of the twisted flexible shaft to that of the individual wires is about three to one, so the loose ensemble would have about one third the friction in a similarly curved sheath. This result is valid for the comparison of two very similar bundles of seven wires: one twisted tightly to form a flexible shaft and one loosely assembled into an ensemble. (Note that this analysis assumes the stiffness of the flexible shaft is equal to the sum of the stiffnesses of its individual wires, which is a very conservative assumption.)

From the foregoing analyses it is seen that there are three non-obvious advantages to using a loosely-twisted (or non-twisted) ensemble of wires as a torque-transmitting shaft versus using a similar tightly-twisted bundle of wires forming a traditional flexible shaft. First, there is greatly reduced hysteresis in a loose ensemble versus a tightly-twisted flexible shaft. Second, the friction (for small angles of rotation) of a loose ensemble in a sheath is a fraction of the friction of an equivalent tightly-twisted flexible shaft. Third, the loose ensemble can wrap around a smaller radius than the tightly-twisted bundle.

The multifilar flexible rotary shaft of the invention has practical uses in many different applications.

Description of Practical Applications Utilizing the Invention:

One practical application for the invention is in the snare instrument of the previously incorporated co-owned application. Turning now to FIGS. 4-7, a surgical snare instrument 210 includes an elongate flexible tubular sheath 212 having a proximal end 214 and a distal end 216, a flexible rotatable shaft 218 having a proximal end 220 and a distal end 222 extending through and axially movable relative to the sheath 212, a snare 224 coupled to or formed at the distal end 222 of the shaft 218, preferably adjacent the distal end 216 of the sheath 212, and first and second handle assemblies 226, 228, respectively, for moving the shaft 218 relative to the sheath 212.

Figure 4:
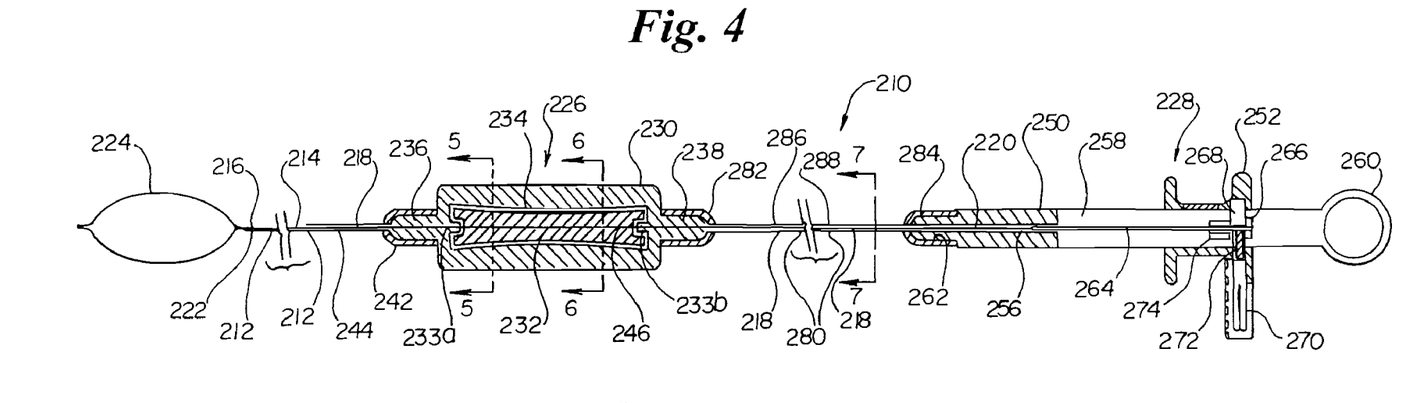
FIG. 4 is broken side elevation in section of a snare instrument utilizing a multifilar flexible rotary shaft according to the invention.
Figures 5, 6:
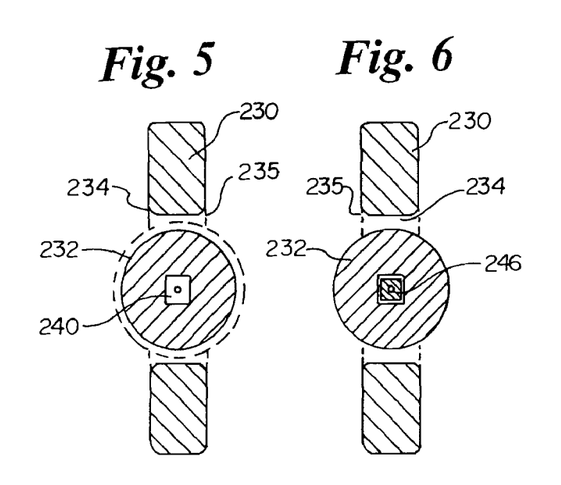
FIG. 5 is an enlarged cross-section taken through line 5-5 in FIG. 4.
FIG. 6 is an enlarged cross-section taken through line 6-6 in FIG. 4.
Figure 7:
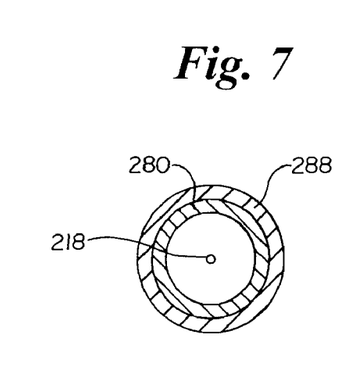
FIG. 7 is an enlarged cross-section taken through line 7-7 in FIG. 4.

The rotatable shaft 218 is preferably made from three high strength, straightened (camber-free) stainless steel wires of high elastic limit, each being approximately 0.012" diameter. The proximal ends of the wires are welded to each other and the distal ends of the wires are welded to each other. Between their proximal and distal ends, the wires are loosely associated. The shaft 218 is adapted to be bent through a tortuous path (e.g., through a radius of approximately 0.8 inches) without permanent deformation. In addition, for the reasons described above, it is possible to precisely rotate the snare 224 by rotating the shaft 218 at any point along its length.

The physician's handle assembly 226, which is the more distal of the two handles, generally includes a body 230 and a knob 232 mounted in the body 230 on bearings 233a, 233b in a manner which permits the knob 232 to rotate coaxially relative to the body. The body 230 includes a central bore 234 with one or more apertures 235, a threaded distal end 236, and a threaded proximal end 238. The sheath 212 of the snare instrument 210 is connected to the threaded distal end 236 of the body 232, e.g., by means of a flare-nut connection 242. Preferably, a stiffening sleeve 244 is provided over the sheath 212 at the connection 242. The knob 232 includes a non-circular bore 240, e.g., having the cross-sectional shape of a square. The knob 232 (for reasons discussed below) is preferably at least as long as the distance of movement required to open and close the snare 224; i.e., the length of the snare when compressed in the sheath 212. The apertures 235 provide access to the knob 232, so that the knob 232 can be rotated relative to the body 230, e.g., by a physician.

A portion of the shaft 218 (preferably the proximal ends of the wires which are bound to each other) extending through the bore 240 of the knob 232 is provided with a key 246; that is, a spline element fixed on and about the shaft 218 or, alternatively, rigidly and fixedly interposed between two portions of the shaft. The key 246 preferably has a rectangular shape but may have another non-circular shape. The key 246 is slidably axially movable within the bore 240. Therefore, the shaft 218 may be moved axially through the bore 240 (and that is why the length of the knob 232 is preferably at least as long as the distance of movement required to open and close the snare). However, when the knob 232 is rotated relative to the body 230, the key 246 within the bore 240 is rotated and, consequently, the shaft 218 and snare 224 are rotated relative to the sheath 212.

The distal handle assembly 226 is preferably positioned approximately 210 cm from the distal end 216 of the sheath 212 for a snare instrument 210 designed to be inserted into a 200 cm endoscope. Thus, the physician can grip the body 230 in a manner which permits rotating the knob 232 relative to the body, and hence the snare 224 relative to the sheath 212, while using the body 230 as a grip to axially position the snare instrument 210 within the working channel of an endoscope.

The shaft 218 extends out of the proximal end 238 of the body 320 to the proximal handle assembly 228, or assistant handle. The proximal handle assembly 228 preferably includes a stationary member 250 and a spool member 252 slidable relative to the stationary member. The stationary member 250 includes a longitudinal throughbore 256 through which the proximal end 220 of the shaft 218 extends, a transverse slot 258, a proximal thumb ring 260, and a distal threaded connector 262. The proximal end of the shaft 218 is preferably provided with a conductive stiffening sleeve 264, and a cylindrical conductive bearing 266 is coupled about the proximal end of the stiffening sleeve 264. The spool member 262 includes a cross bar 68 which extends through the transverse slot 258 to secure the spool member 252 on the stationary member 250. In addition, the spool member 262 preferably includes a cautery plug 270. The conductive bearing 266 extends through the cross bar 268 and a collar 274 secures the bearing 266 in the cross bar 268 in a manner which permits the conductive bearing to freely rotate within the cross bar 268. A spring 272 extends between the cautery plug 270 and the conductive bearing 266, and provides a contact between the plug 270 and the bearing 266 regardless of the rotational position of the bearing 266. Movement of the spool member 252 relative to the stationary member 250 causes the snare 224 to extend from and retract into the distal end 216 of the sheath 212. Those skilled in the art will appreciate that since the portion of the shaft between the proximal and distal handles is not likely to traverse a tortuous path (between the physician and the assistant) it may be made of a monofilar wire or some other flexible shaft which is not as flexible as that in the portion distal to the distal handle.

As described in the previously incorporated application, an electrically insulative extension sheath 280 extends over the shaft 218 between the proximal end 238 of the body 230 and the distal end 262 of the stationary member 250, coupled, e.g., via flare-nut connections 282, 284. Thus, there is a continuous outer connection joining, yet spacing apart, the distal handle assembly 226 and the proximal handle assembly 228. A stiffening sleeve 286 is preferably provided over the extension sheath 280 at the proximal end 238 of the body 230, and another stiffening sleeve 288 is preferably provided over the extension sheath 280 at the distal end 262 of the stationary member 250.

In use, the physician introduces the snare instrument 210 into the endoscope (not shown), typically by means of a port in the endoscope handle which communicates with the working channel of the endoscope. Then, the physician gives the proximal assistant's handle 228 to the assistant. The physician then grips the body 230 of the distal physician's handle 226 of the snare instrument and uses it to position the distal end 216 of the sheath 212 adjacent to the polyp to be excised. The physician then instructs the assistant to extend the snare, which is performed by moving the spool member 252 relative to the stationary member 250. The physician then uses the distal handle 226 to simultaneously axially position and rotate the snare over the polyp by rotating the shaft 218 via the knob 232. Then, the physician instructs the assistant to close the snare and sever the polyp, using cautery if desired. In this manner, the physician controls the means of positioning the snare onto the polyp, and the assistant controls the opening and closing of the snare and the cauterization.

Another practical application for the invention is in the microsurgical cutting instruments disclosed in U.S. Pat. No. 5,439,478, the complete disclosure of which is hereby incorporated by reference herein.

Figure 8:
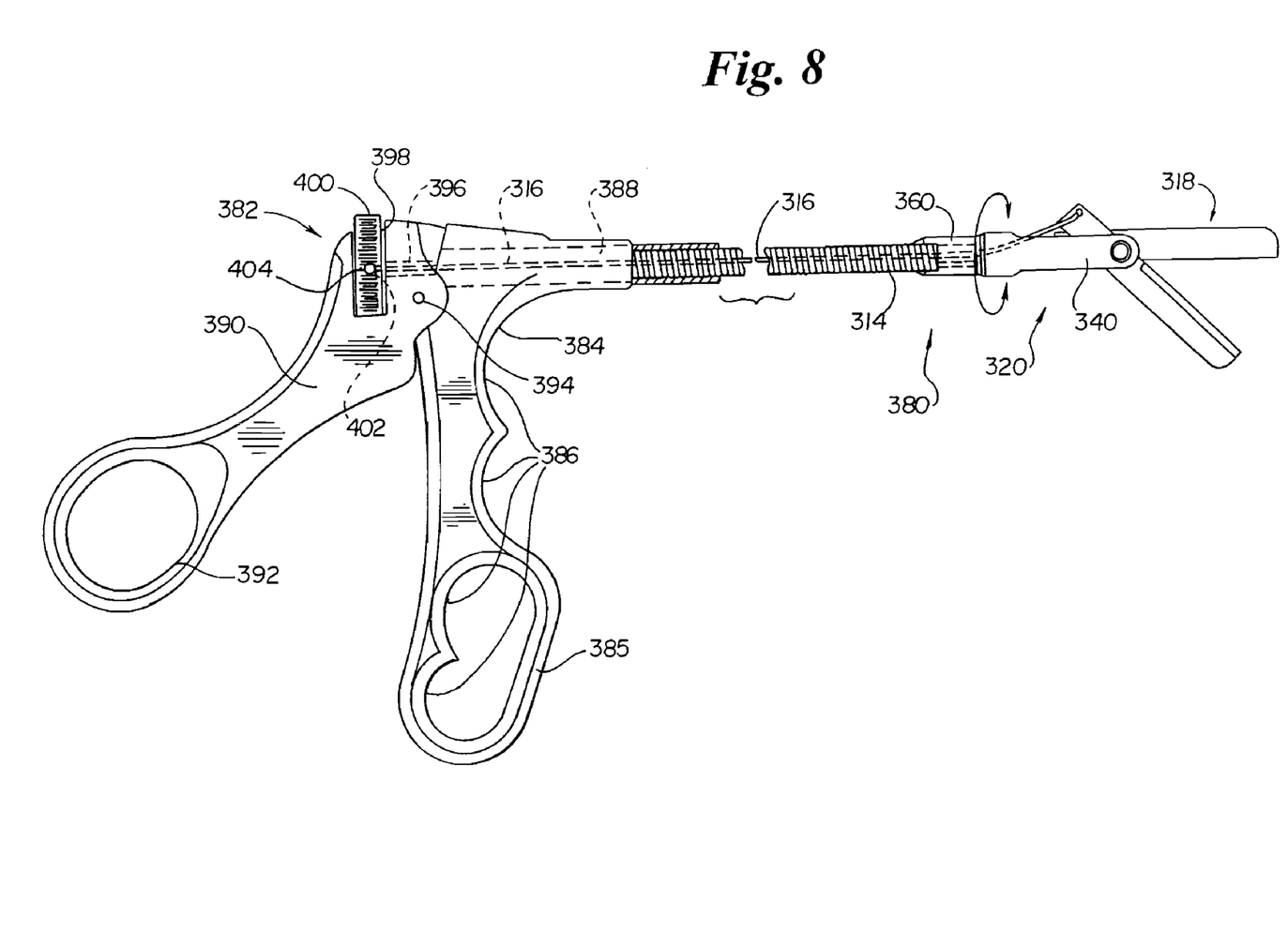
FIG. 8 is a side elevation view in partial longitudinal section of a microsurgical cutting instrument utilizing a multifilar flexible rotary shaft according to the invention.

Referring now to FIG. 8, a microsurgical instrument 380 incorporating the invention includes a flexible coil 314, a flexible rotatable shaft 316 extending through the coil 314, distal end effectors 318 coupled to the shaft 316, a rotatable clevis assembly 320 which is coupled to the distal end of the coil 314, and a proximal actuation assembly 382. The proximal actuation assembly 382 has a stationary handle portion 384 which is provided with finger recesses 386, two of which are covered by a finger ring 385, and a throughbore 388 for receiving the coil 314 and flexible rotatable shaft 316. A lever arm 390 having a thumb ring 392 is pivotally attached to the stationary handle 384 by a pivot axle 394. The lever arm 390 has a bore 396 which is substantially coaxial with the bore 388 in the stationary handle and a slot 398 which is substantially orthogonal to the bore 396. The slot 398 is fitted with a knurled disk 400 having a shaft receiving bore 402 and a set screw 404.

The proximal end of the coil 314 is mounted within the throughbore 388 of the stationary handle 384 by crimping, soldering, pressure fit or other suitable method. The proximal end of the flexible rotatable shaft 316 is inserted into the bore 402 of the disk 400 and held in place by the set screw 404. Those skilled in the art will appreciate that the shaft 316 is therefore rotatable relative to the actuation assembly 382 by rotation of the knurled disk 400 inside the slot 398 in the lever arm 390. It will also be appreciated that movement of the lever arm 390 relative to the stationary handle 384 will cause a translational movement of the shaft 316 relative to the coil to open and close the end effectors 318.

According to the invention, the flexible rotatable shaft 316 is made from three stainless steel wires, each having a diameter of 0.012 inches. The proximal ends of the wires are welded to each other at the shaft receiving bore 402 and the distal ends of the wires are welded to each other at the end effectors 318. Between their proximal and distal ends, the wires are not tightly wound together, and are preferably not wound together at all. The typical length of the shaft 316 is approximately 100-250 cm. The shaft will accurately transmit a torque of approximately 0.03 ounce-inches. The shaft 316 is capable of traversing a bend having a radius of 0.08 inches.

In operation, the practitioner holds the actuation assembly 382 with fingers wrapped around the recesses 386 and with the thumb inserted in the thumb ring 392. The index finger is free to rotate the disk 400 which effects a rotation of the shaft 316 and thus a rotation of the clevis 340 and end effectors 318.

Those skilled in the art will appreciate that the present invention is advantageously used in conjunction with the other embodiments disclosed in the previously incorporated patents. Moreover, the invention is advantageously used in conjunction with other steerable surgical instruments including forceps, baskets, ablators, crushers and drillers. The invention is also advantageously used in conjunction with cardiovascular instruments including blood pumping instruments which utilize a flexible rotatable shaft, steerable forceps, rotary catheters, steerable electrodes, steerable injection needles, and steerable cautery devices. In addition to various endoscopic instruments, the invention is advantageously utilized in conjunction with various laparoscopic instruments such as: catheters for cannulating the fallopian tubes/uterus, steerable scissors, graspers, dissectors and cautery probes, resection devices, and ablation devices. The invention is also advantageously used in other steerable devices such as guidewires. In addition to surgical devices, the invention finds useful application in such unrelated arts as miniature flexible shafts for control or power transmission, aircraft control cables, remote instruments such as compasses and wind direction instruments, dental drills, speedometer drive cables, and steerable inspection scopes.

There have been described and illustrated herein several examples of a multifilar flexible rotary shaft. While particular embodiments and applications of the invention have been described, it is not intended that the invention be limited thereto, as it is intended that the invention be as broad in scope as the art will allow and that the specification be read likewise. Thus, while particular dimensions have been disclosed, it will be appreciated that other dimensions could be utilized. Also, while a particular number of filaments have been shown, it will be recognized that the number of filaments will be determined by the application. Moreover, while particular configurations have been disclosed in reference to welding the ends of the filaments, it will be appreciated that other means for binding the ends together could be used as well. It will therefore be appreciated by those skilled in the art that yet other modifications could be made to the provided invention without deviating from its spirit and scope as so claimed.

What is claimed is:

1. A surgical instrument for insertion through a medical device having a handle and a working channel, said surgical instrument comprising:
   a elongate flexible tubular sheath having proximal and distal ends;
   a flexible shaft extending through and axially movable relative to the sheath, said shaft having proximal and distal ends;
   an end effector coupled to or formed at said distal end of said shaft;
   a first handle assembly positioned distally of the proximal end of the shaft;
   a second handle assembly coupled to the proximal ends of the tubular sheath and flexible shaft;
   wherein the first handle assembly includes a rotatable knob having a bore formed therein;
   wherein a key member is attached to the shaft;
   wherein the key member has a non-circular cross-sectional shape;
   wherein the key member is disposed within the bore and is axially movable within the bore; and
   wherein said flexible shaft includes a plurality of individual wire filaments, each having an input end and an output, the input end of each individual wire filament being coupled to the input end of each other individual wire filament, the output end of each individual wire filament being coupled to the output end of each other individual wire filament, and between their input ends and their output ends, said individual wire filaments are loosely associated.

2. A surgical instrument according to claim 1, wherein between their input ends and their output ends, said individual wire filaments are not twisted about each other.

3. A surgical instrument according to claim 1, wherein between their input ends and their output ends, said individual wire filaments are loosely twisted about each other.

4. A surgical instrument according to claim 1, wherein between their input ends and their output ends, said individual wire filaments are loosely braided.

5. A surgical instrument according to claim 1, wherein said individual wire filaments are substantially identical to each other and each has a diameter of between approximately 0.005 inches to 0.040 inches.

6. A surgical instrument according to claim 1, wherein said shaft is capable of accurately transmitting a torque on the order of 0.1 ounce-inches through an operational radius of approximately 0.8 inches.

* * * * *